(12) United States Patent
Jun (10) Patent No.: US 11,344,642 B2
(45) Date of Patent: May 31, 2022

(54) HOME PLASMA STERILIZER (71) Applicant: JUNSYS CO., LTD., Gwangmyeong-si (KR)

(72) Inventor: DeokSoo Jun, Gwangmyeong-si (KR)

(73) Assignee: JUNSYS CO., LTD., Gwangmyeong-si (KR)

( * ) Notice: Subject to any disclaimer, the term of this patent is extended or adjusted under 35 U.S.C. 154(b) by 289 days.

(21) Appl. No.: 16/762,185

(22) PCT Filed: Nov. 21, 2018

(86) PCT No.: PCT/KR2018/014322
§ 371 (c)(1),
(2) Date: May 7, 2020

(87) PCT Pub. No.: WO2019/103444
PCT Pub. Date: May 31, 2019

(65) Prior Publication Data
US 2020/0360550 A1 Nov. 19, 2020

(30) Foreign Application Priority Data

Nov. 23, 2017 (KR) .................. 10-2017-0157488

(51) Int. Cl.
A61L 2/14 (2006.01)
A61L 101/26 (2006.01)
(52) U.S. Cl.
CPC ............ A61L 2/14 (2013.01); A61L 2101/26 (2020.08); A61L 2202/11 (2013.01); A61L 2202/122 (2013.01); A61L 2202/14 (2013.01); A61L 2202/20 (2013.01)

(58) Field of Classification Search
CPC .. A61L 2/14; A61L 2202/11; A61L 2202/122; A61L 2202/14; A61L 2202/20
See application file for complete search history.

(56) References Cited

U.S. PATENT DOCUMENTS

2004/0037736 A1* 2/2004 Perruchot ............... A61L 2/24
422/4

FOREIGN PATENT DOCUMENTS

| CN | 102510596 A | 6/2012 |
| CN | 203634532 U | 6/2014 |
| KR | 10-2000-0030560 A | 6/2000 |

(Continued)

Primary Examiner — Timothy C Cleveland
(74) Attorney, Agent, or Firm — KORUS Patent, LLC; Seong Il Jeong (57) ABSTRACT The following disclosure relates to a home plasma sterilizer that sterilizes household items in a home by using plasma. According to an embodiment, there is provided a home plasma sterilizer including: a plurality of plasma electrode modules configured to generate plasma in order to sterilize a sterilization target object inside a sterilization chamber; a harmful gas removal unit configured to communicate with the sterilization chamber, and provided with a catalytic filter that is intended to remove harmful gas inside the sterilization chamber; a power supply unit configured to supply power to the plasma electrode modules; and a control unit configured to control the supply of power by the power supply unit; wherein the control unit performs control so that the plurality of plasma electrode modules is sequentially supplied with power at predetermined cycles but the supply of power is continuous as a whole.

4 Claims, 6 Drawing Sheets (56) References Cited

FOREIGN PATENT DOCUMENTS

| KR | 10-2004-0101806 A | 12/2004 |
| KR | 10-2010-0082614 A | 7/2010 |
| KR | 10-1012442 B1 | 2/2011 |
| KR | 10-1388004 B1 | 4/2014 |
| KR | 10-1837132 B1 | 3/2018 |

* cited by examiner

HOME PLASMA STERILIZER

TECHNICAL FIELD

The following disclosure relates to a home plasma sterilizer that sterilizes household items in a home by using plasma.

BACKGROUND ART

In recent years, as various infectious diseases have occurred, the importance of technology for preventing such diseases has risen. In particular, infants and the elderly with relatively weak immunity may be easily infected when exposed to pathogens, and thus there is increasing interest in sterilizers that are capable of easily sterilizing household items that are used in homes.

Conventionally, sterilizers using high-temperature steam or sterilizers using ultraviolet rays are chiefly used. In the former cases, there was a risk of a user being burned, and some plastics or synthetic resin household items were restricted in use due to harmfulness to the human body. In the latter cases, due to the characteristics of ultraviolet rays, disadvantages arise in that a dead zone is generated, so that a sterilization effect is reduced and it takes a long time to sterilize a household item.

In order to overcome these problems, recently, various plasma sterilizers, such as a sterilizer using atmospheric pressure plasma disclosed in Korean Patent No. 10-1012442, have been disclosed. However, in the case of the conventional plasma sterilizers, excessive energy is concentrated on a discharge electrode as plasma is generated by successively applying high-voltage current to a single plasma generation electrode in order to increase a sterilization effect, with the result that a problem occurs in that high heat is generated and also chemical reaction having a negative effect on the electrode is accelerated, so that the electrode is lost.

DISCLOSURE

Technical Problem

The present invention has been conceived to overcome the above-described problems, and an object of the present invention is to provide a home plasma sterilizer that has improved lifespan and improved sterilization performance.

Another object of the present invention is to provide a home plasma sterilizer that can be fabricated at low cost.

Technical Solution

According to an embodiment, there is provided a home plasma sterilizer including: a plurality of plasma electrode modules configured to generate plasma in order to sterilize a sterilization target object inside a sterilization chamber; a harmful gas removal unit configured to communicate with the sterilization chamber, and provided with a catalytic filter that is intended to remove harmful gas inside the sterilization chamber; a power supply unit configured to supply power to the plasma electrode modules; and a control unit configured to control the supply of power by the power supply unit; wherein the control unit performs control so that the plurality of plasma electrode modules is sequentially supplied with power at predetermined cycles but the supply of power is continuous as a whole.

In this case, the plasma electrode modules may include four, and may be symmetrically disposed on the top, bottom, left, and right sides of the sterilization chamber, respectively.

Furthermore, each of the plasma electrode modules may include a substrate made of a dielectric material and discharge and induction electrodes, and the substrate may be made of FR-4 material.

Meanwhile, the catalyst of the catalytic filter may include 18 to 26 mol % of copper oxide ($CuO$) and 74 to 82 mol % of manganese dioxide ($MnO_2$).

Advantageous Effects

According to the disclosure, effects are achieved by improving the plasma electrode modules in that the lifespan is extended and sterilization performance is increased.

Furthermore, effects are achieved in that the sterilizer can be manufactured at low cost and harmful gas in the sterilization chamber can be effectively removed.

The effects of the present invention are not limited to the effects mentioned above, and other effects not mentioned will become apparent to those skilled in the art from the description of the claims.

DESCRIPTION OF REFERENCE SYMBOLS

10: housing 12: door
14: support frame 100: sterilization chamber
120: plasma electrode module 122: substrate
124: discharge electrode 126: induction electrode
140: harmful gas removal unit 142: catalytic filter
144: blower fan 160: plasma power supply unit
180: control unit

Mode for Invention

A home plasma sterilizer according to preferred embodiments will be described in detail below with reference to the accompanying drawings.

Figure 1:
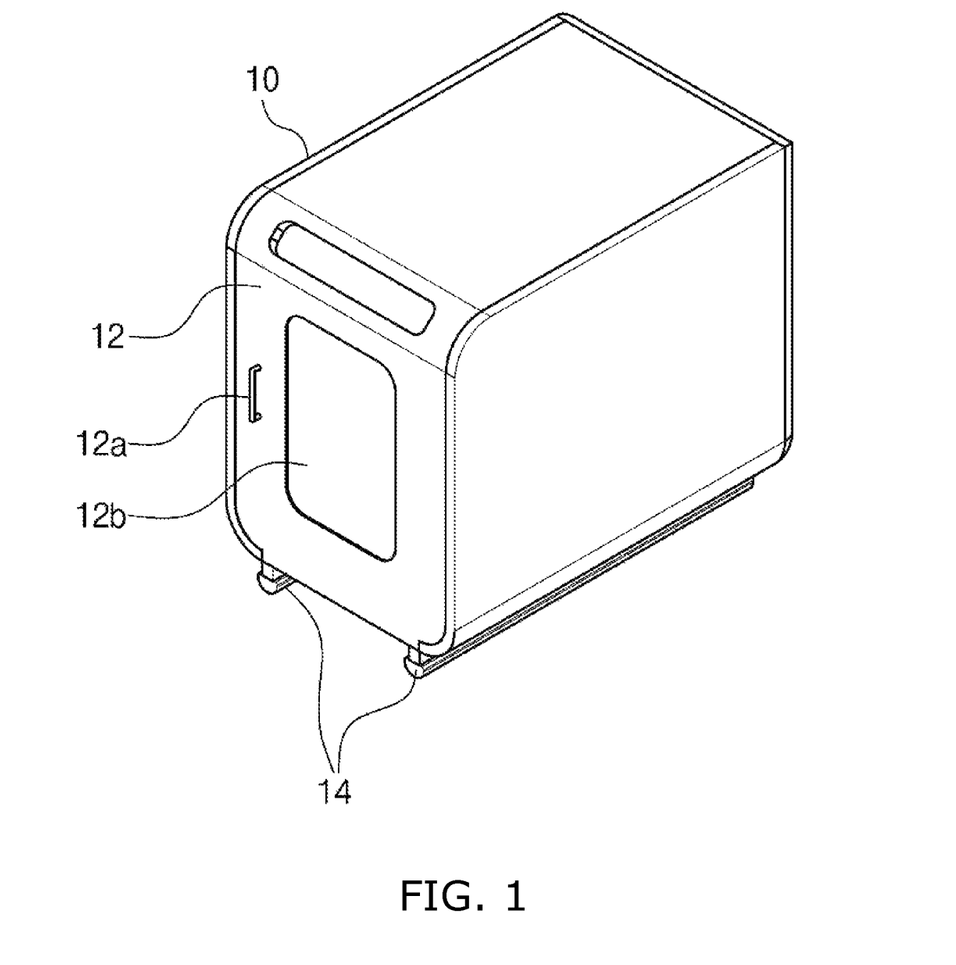
FIG. 1 is a perspective view of a home plasma sterilizer according to an embodiment.

FIG. 1 is a perspective view of a home plasma sterilizer according to one embodiment.

Referring to FIG. 1, the home plasma sterilizer according to the present embodiment may include a housing 10 configured to accommodate main components such as a sterilization chamber therein, a door 12 configured to open or close a sterilization chamber 100 (see FIG. 2) in response to the opening or closing in order to process a sterilization target object, and a support frame 14 configured to come into contact with a support surface and support the sterilizer so that the sterilizer is prevented from being moved laterally.

Although the housing 10 may be formed in various shapes, the housing 10 is preferably formed in a box shape so that a sterilization target object may be easily put into and taken from the housing 10. Meanwhile, the door 12 may be provided with a grip 12a for the purpose of easy opening and closing, and a transparent window 12b may be installed at the center of the door 12 to see the inside of the sterilization chamber 100.

Figure 2:
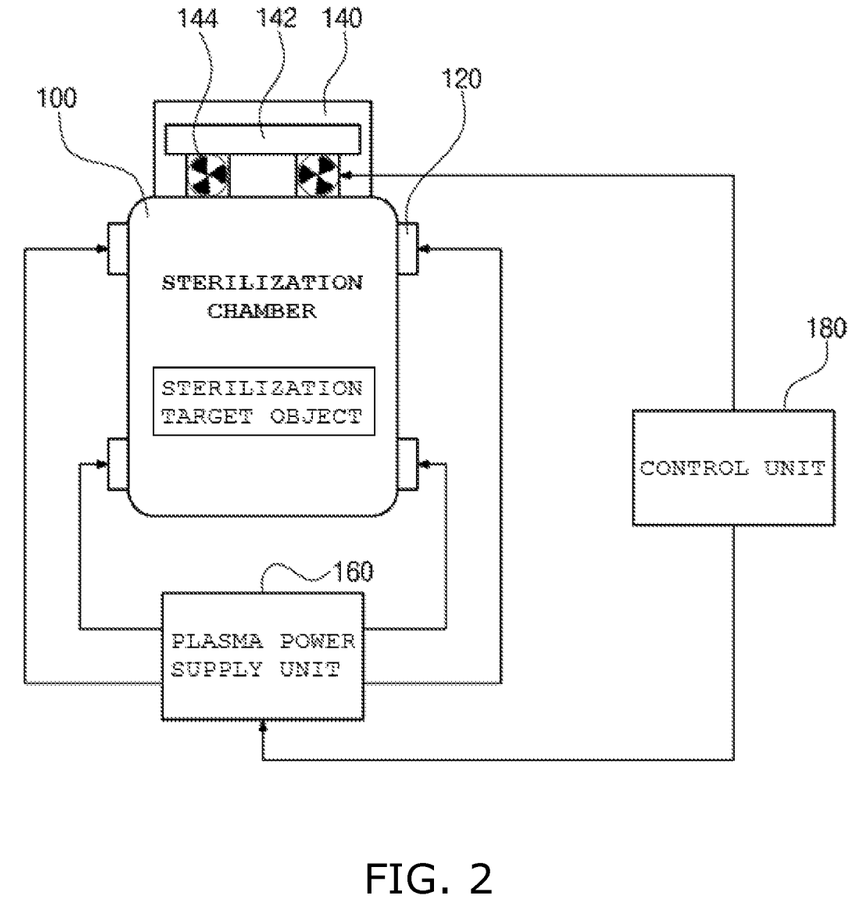
FIG. 2 is a block diagram schematically showing the inside of FIG. 1.
Figure 3A:
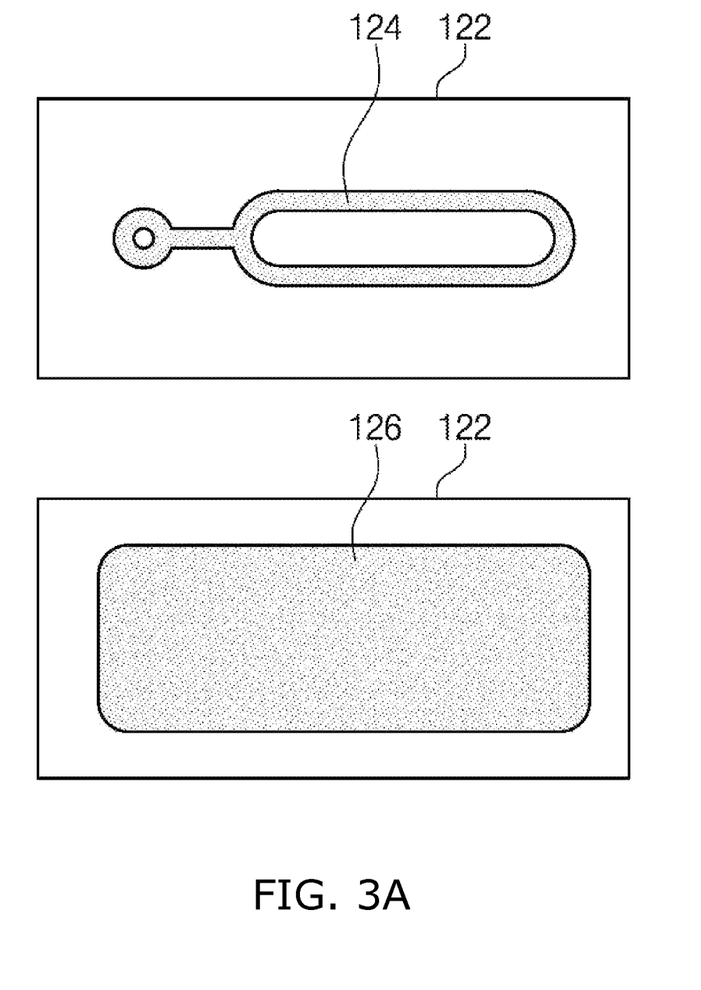
FIG. 3a is a view showing an example of the top and bottom surfaces of the plasma electrode module shown in FIG. 2.
Figure 3B:
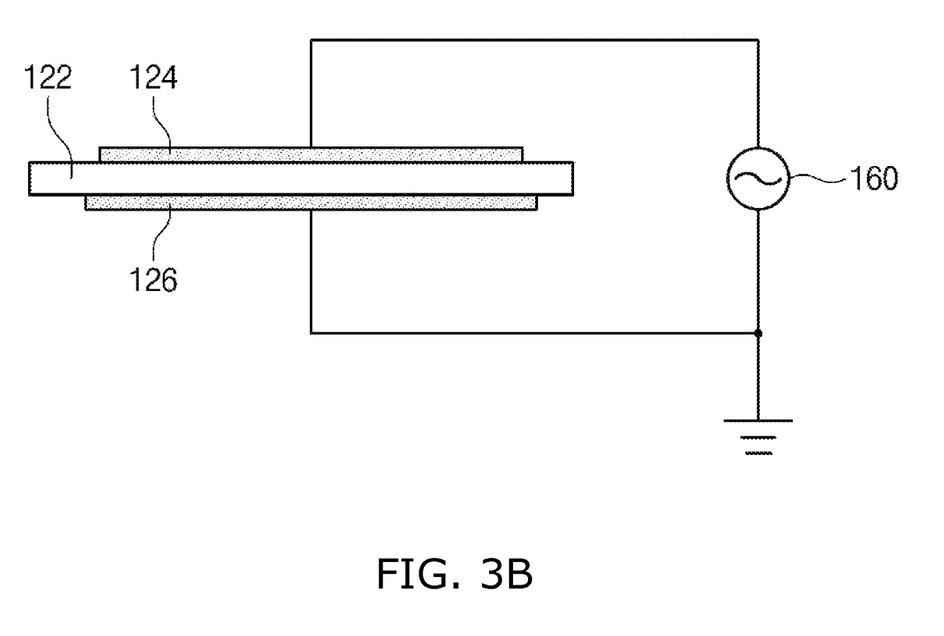
FIG. 3b is a sectional view of the plasma electrode module shown in FIG. 2.

FIG. 2 is a block diagram schematically showing the inside of FIG. 1, FIG. 3a is a view showing an example of the top and bottom surfaces of the plasma electrode module shown in FIG. 2, and FIG. 3b is a sectional view of the plasma electrode module shown in FIG. 2.

Referring to FIG. 2, the home plasma sterilizer according to the embodiment includes the sterilization chamber 100, a plurality of plasma electrode modules 120, a harmful gas removal unit 140, a power supply unit 160, and a control unit 180.

The sterilization chamber 100 is a chamber for locating therein a sterilization target object, such as a household item, used in a home and sterilizing it, is provided with an opening (not shown) on one side thereof, and is opened or closed in response to the opening or closing of the door 12. Although the sterilization chamber 100 is preferably formed in a box shape, as shown in FIG. 2, it is not limited thereto but may be formed in various shapes such as a spherical shape, a cylindrical shape, or the like.

The plasma electrode module 120 is a device for generating plasma in the atmospheric pressure state of the inside of the sterilization chamber 100, and includes a substrate 122 made of a dielectric material, an induction electrode 126 provided on the bottom surface of the substrate 122, and a discharge electrode 124 provided on the top surface and configured to generate plasma discharge by high-voltage power. In this case, although the substrate 122 may be one of the substrates made of various dielectric materials, it is preferably made of a fiberglass-based FR-4 substrate that has excellent insulation and is relatively inexpensive. Conventionally, polytetrafluoroethylene (PTFE) or ceramic dielectric substrates are mainly used, but have problems in that the dielectric constants thereof are low and manufacturing costs are expensive due to the high prices thereof. Furthermore, the substrate 122 is preferably formed to have a thickness of 0.4 mm so that it can withstand high-voltage power and plasma discharge can be generated desirably.

The plurality of plasma electrode modules 100 are symmetrically arranged with respect to each other based on the inner center of the sterilization chamber 100. Preferably, the plurality of plasma electrode modules 100 may include four, and may be symmetrically disposed on the top, bottom, left, and right sides of the sterilization chamber 100, respectively. In this case, advantages arise in that plasma may be evenly spread over a sterilization target object in the sterilization chamber 100 and the power supply efficiency of the power supply unit 160 to be described later may be increased. Meanwhile, when the capacity of the sterilizer is large and the generation of a larger amount of plasma is required, a plurality of sets of two or more plasma electrode modules may be provided.

The power supply unit 160 functions to supply power to the plurality of plasma electrode modules 120 under the control of the controller 180, and transmits high-voltage power to generate plasma in an atmospheric pressure state.

A detailed description of a power supply and application method that is performed by the controller 180 will be described later.

The harmful gas removal unit 140 communicates with the sterilization chamber 100, includes a catalytic filter 142 for removing harmful gas in the sterilization chamber 100, and may further include a blower fan 144 for moving air, in which harmful gas in the sterilization chamber 100 is contained, to the catalyst filter 142. When plasma is generated by high voltage in the sterilization chamber 100, harmful gas such as ozone or nitrogen oxide is entailed. At this time, the air containing the harmful gas is moved to the harmful gas removal unit 140 by the blower fan 144, in which case the air is purified by the catalyst of the catalytic filter 142 and then returned to the chamber 100 by the blower fan 144.

In this case, the catalyst used may include 18 mol % or more of copper oxide (CuO) and 74 mol % or more of manganese dioxide ($MnO_2$) as main components and also include a small amount of aluminum oxide ($Al_2O_3$). However, in order to maximize the ozone decomposition rate of the catalyst, it is preferable that the catalyst includes 18 to 26 mol % of copper oxide (CuO) and 74 to 82 mol % of manganese dioxide ($MnO_2$). Meanwhile, the catalyst may be formed in various shapes but is preferably formed into pellets having a diameter of about 3 mm in order to maximize catalytic efficiency.

Figure 4:
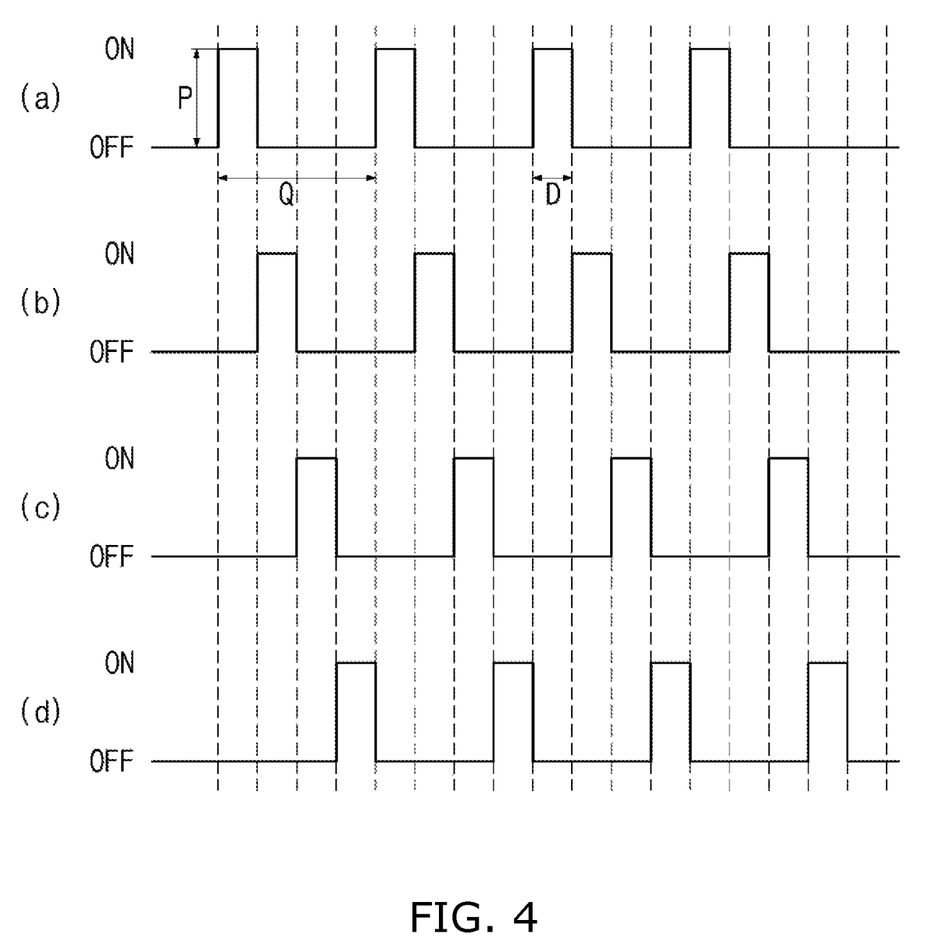
FIG. 4 is a view showing an example of a method of applying power to the plasma electrode modules shown in FIG. 2.

FIG. 4 is a view showing an example of a method of applying power to the plasma electrode modules shown in FIG. 2. For reference, FIGS. 4(a) to 4(d) show power supply waveforms showing states in which power is supplied to the four electrode modules shown in FIG. 2. In FIG. 4(a), P is the voltage, Q is the period, and D is the duty ratio.

Referring to FIG. 4, the control unit 180 performs control so that the plurality of plasma electrode modules 120 is sequentially supplied with power at predetermined cycles but the supply of power is continuous as a whole. For example, as shown in FIG. 4, when power is turned on to the first plasma electrode module 120, the other three plasma electrode modules 120 enter an OFF state in which power is not applied thereto. When the power applied to the first plasma electrode module 120 is turned off after a predetermined period of time, power is supplied to the next second plasma electrode module 120, and at this time the remaining three plasma electrode modules enter an OFF state in which power is not applied thereto. In this manner, the third and fourth plasma electrode modules 120 are sequentially supplied with power. According to this method, the plasma electrode modules 120 are supplied with power at predetermined cycles. When viewed via the plasma electrode modules 120 as a whole, the supply of power is continuous, and plasma is continuously generated inside the sterilization chamber 100.

According to the above-described configuration, there can be prevented the generation of high heat and the leakage of power attributable to excessive energy concentration when power is continuously applied to a single or multiple plasma electrode modules 120 at the same time, thereby providing the effect of extending the lifespan of the sterilizer. Furthermore, the individual plasma electrode modules 120 may be evenly distributed inside the sterilization chamber 100, thereby providing the effect in which a uniform sterilization effect can be obtained regardless of the loaded location of a sterilization target object.

Figure 5:
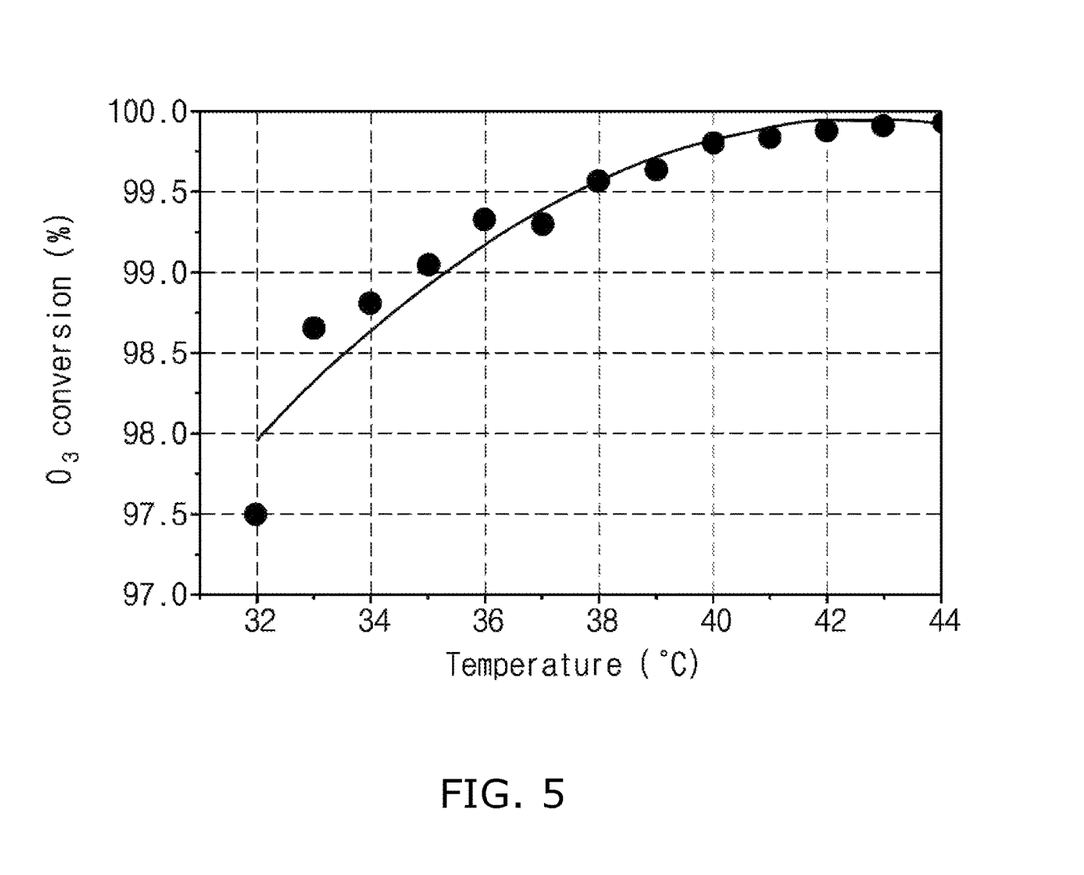
FIG. 5 is a graph showing the ozone decomposition rates of a catalyst, which is a component of the harmful gas removal unit shown in FIG. 2.

FIG. 5 is a graph showing the ozone decomposition rates of a catalyst, which is a component of the harmful gas removal unit shown in FIG. 2.

FIG. 5 shows the decomposition rates of ozone when the catalyst is configured to contain 18 to 26 mol % of copper oxide (CuO) and 74 to 82 mol % of manganese dioxide ($MnO_2$). As shown in the drawing, a decomposition rate of 97% or more was exhibited in a temperature condition of 32° C. or higher, and a decomposition rate of almost 100% was exhibited in the case of 40° C. or higher. This indicates that the decomposition rates are significantly higher under the same conditions than those of a typical high-temperature decomposition method using heater heating, a method using only manganese dioxide as a catalyst, and a decomposition method using activated carbon as an adsorbent. Accordingly, the plasma sterilizer according to the preferred embodiment has the advantages of having an excellent decomposition rate for harmful gas such as ozone and enabling rapid purification.

While the preferred embodiments of the present invention have been described above with reference to the accompanying drawings, the embodiments described in the present specification and the configurations shown in the drawings are merely the most preferred embodiments of the present invention and represent all technical spirits of the present invention. Accordingly, it should be understood that there may be various equivalents and modifications that can replace them at the time when the present application is filed.

INDUSTRIAL APPLICABILITY

The disclosure is applicable to the field of home plasma sterilizers that sterilize household items in homes by using plasma.

The invention claimed is:

1. A home plasma sterilizer comprising:
a sterilization chamber;
a plurality of plasma electrode modules configured to generate plasma in order to sterilize a sterilization target object inside the sterilization chamber;
a harmful gas removal unit configured to communicate with the sterilization chamber, and provided with a catalytic filter that is intended to remove harmful gas inside the sterilization chamber;
a power supply unit configured to supply power to the plasma electrode modules; and
a control unit configured to control the supply of power by the power supply unit;
wherein the control unit performs control so that each of the plurality of plasma electrode modules are sequentially supplied with power at predetermined cycles but the supply of power is continuous as a whole.

2. The home plasma sterilizer of claim 1, wherein the plurality of plasma electrode modules comprise four plasma electrode modules which are symmetrically disposed on top, bottom, left, and right sides of the sterilization chamber, respectively.

3. The home plasma sterilizer of claim 1, wherein each of the plasma electrode modules comprises a substrate made of a dielectric material and discharge and induction electrodes provided on top and bottom surfaces of the substrate, respectively, and the substrate is made of FR-4 material.

4. The home plasma sterilizer of claim 1, wherein a catalyst of the catalytic filter comprises 18 to 26 mol % of copper oxide (CuO) and 74 to 82 mol % of manganese dioxide ($MnO_2$).

* * * * *